(12) United States Patent
Hardcastle et al.

(10) Patent No.: US 6,579,290 B1
(45) Date of Patent: Jun. 17, 2003

(54) SURGICAL IMPLANT AND SURGICAL FIXING SCREW

(75) Inventors: Philip Hobson Hardcastle, Wembley (AU); Duncan Robert Keeble, Worcestershire (GB)

(73) Assignee: Surgicraft Limited (GB)

( * ) Notice: Subject to any disclaimer, the term of this patent is extended or adjusted under 35 U.S.C. 154(b) by 0 days.

(21) Appl. No.: 09/555,398

(22) PCT Filed: Nov. 27, 1998

(86) PCT No.: PCT/GB98/03557

§ 371 (c)(1),
(2), (4) Date: Nov. 9, 2000

(87) PCT Pub. No.: WO99/27864

PCT Pub. Date: Jun. 10, 1999

(30) Foreign Application Priority Data

Nov. 29, 1997 (GB) .............................................. 9725258
Nov. 29, 1997 (GB) .............................................. 9725259

(51) Int. Cl.[7] .............................................. A61B 17/68
(52) U.S. Cl. ...................................... 606/61; 623/17.16
(58) Field of Search ........................ 606/61; 623/17.11, 623/17.16

(56) References Cited

U.S. PATENT DOCUMENTS 4,904,261 A * 2/1990 Dove et al. .............. 623/17.16
6,235,059 B1 * 5/2001 Benezech et al. ........ 623/17.16

FOREIGN PATENT DOCUMENTS

| CH | 672 245 | 11/1989 | |
| DE | 43 28 690 | 3/1995 | |
| DE | 4328690 A1 * | 3/1995 | ........... A61B/17/56 |
| DE | 195 45 612 | 6/1997 | |
| FR | 2 642 958 | 2/1989 | |
| FR | 2747034 A * | 4/1996 | |
| FR | 2 747 034 | 4/1996 | |
| GB | 2 207 607 | 2/1989 | |
| GB | 2207607 A * | 2/1989 | ............. A61F/2/44 |
| WO | WO 94/26193 | 11/1994 | |
| WO | WO 95/31941 | 11/1995 | |
| WO | WO 97/22306 | 6/1997 | |

* cited by examiner

Primary Examiner—John J. Calvert
Assistant Examiner—Shaun R Hurley
(74) Attorney, Agent, or Firm—Cantor Colburn LLP

(57) ABSTRACT

A surgical implant (2) for fusing adjacent vertebrae (V) together comprises a body portion (4) with spaced arms (10). The body portion (4) has passages (16a and 16b) to receive surgical fixing screws (100) engaged in holes drilled in the vertebrae (V) for securing the body portion (4) to the anterior faces of the vertebrae (V) to be fused. The arms (10) extend into a prepared space between the vertebrae to be fused. Graft material is packed between the arms (10). Each surgical fixing screw (100) has an externally screw-threaded shank (101) divided into wings which can be outwardly deformed to anchor the shank (101) in the hole. Each surgical fixing screw (100) also had a head (102) which can be transformed between a laterally expanded condition and a laterally contracted condition to permit the head to be interlocked with the implant (2).

22 Claims, 5 Drawing Sheets

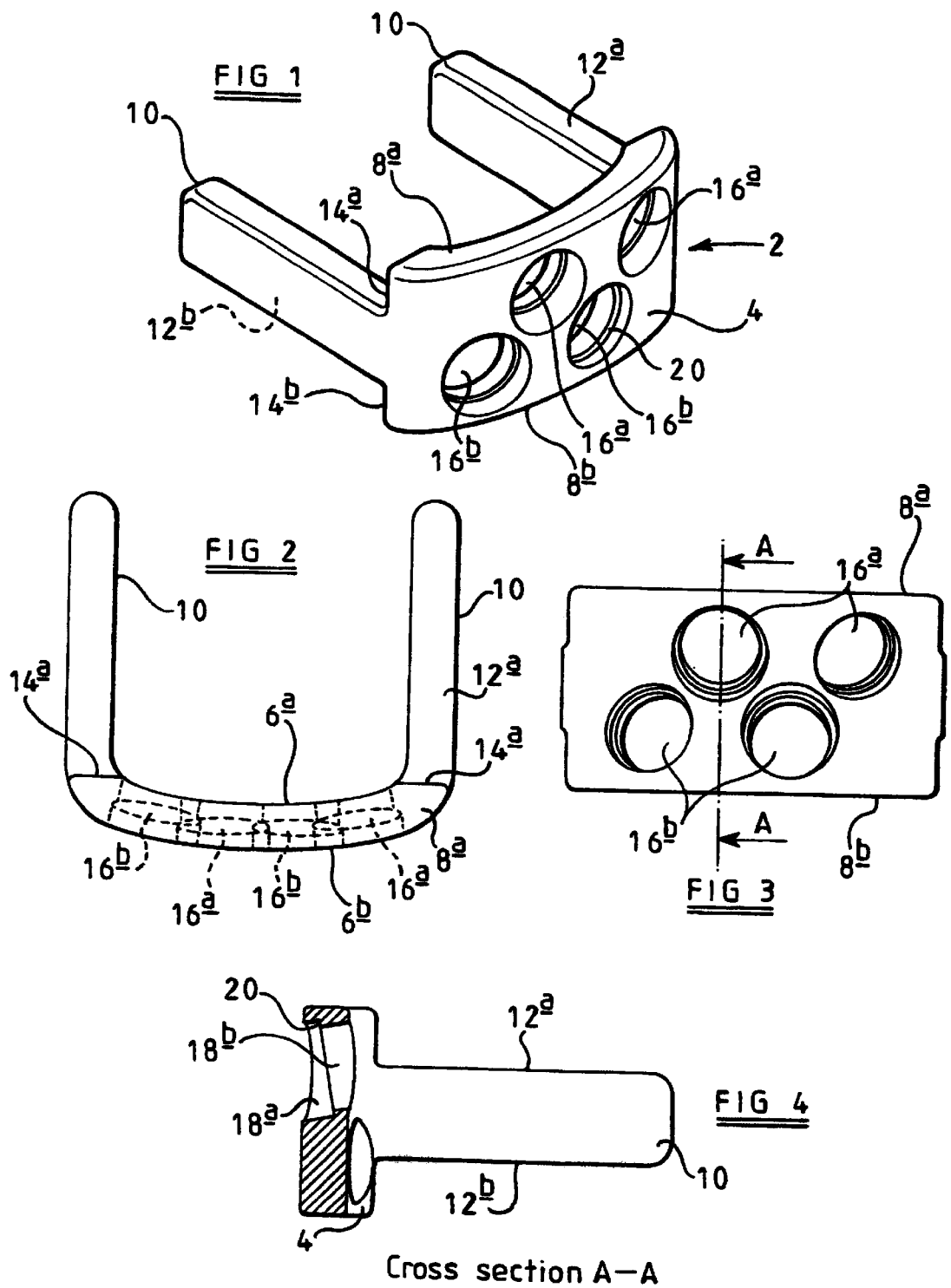

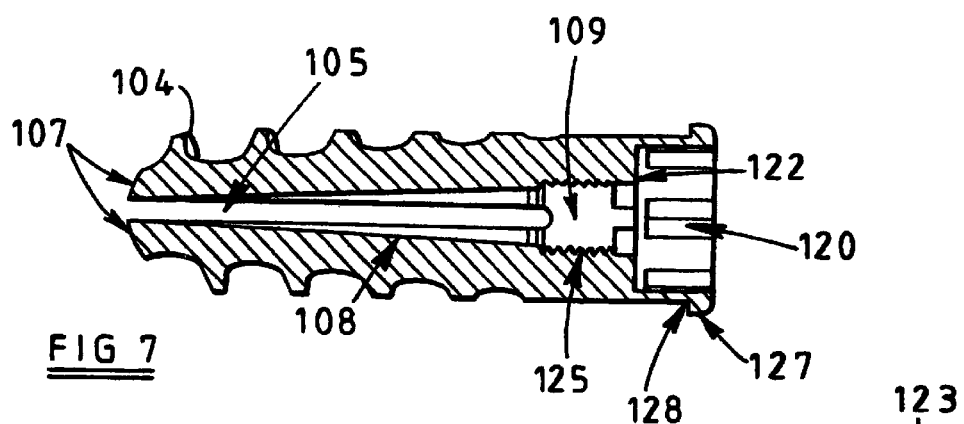
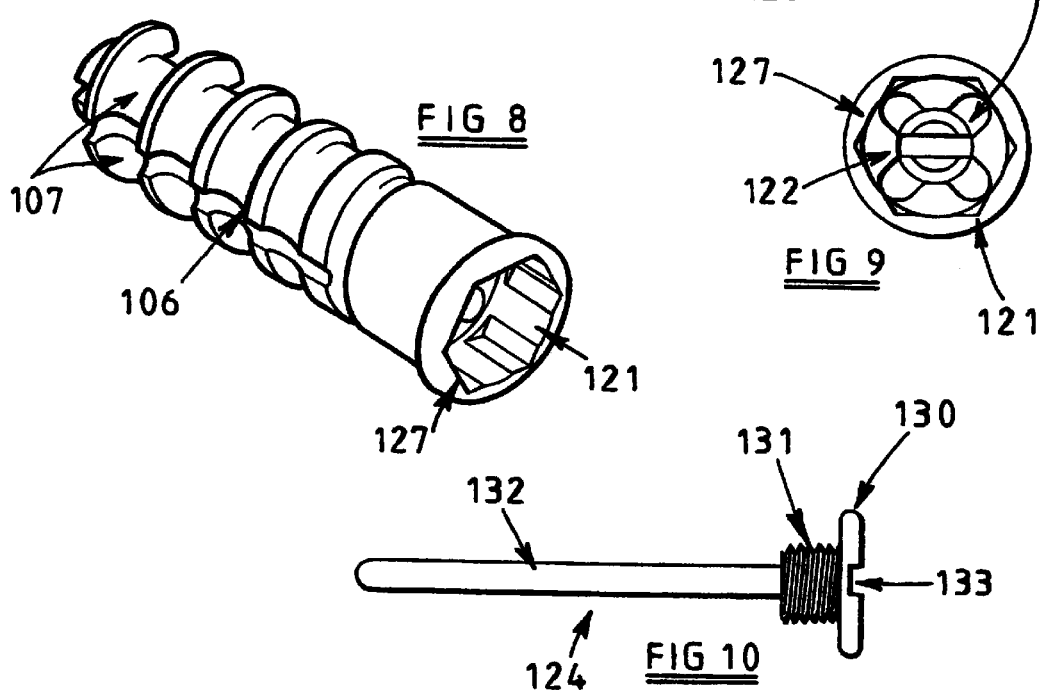
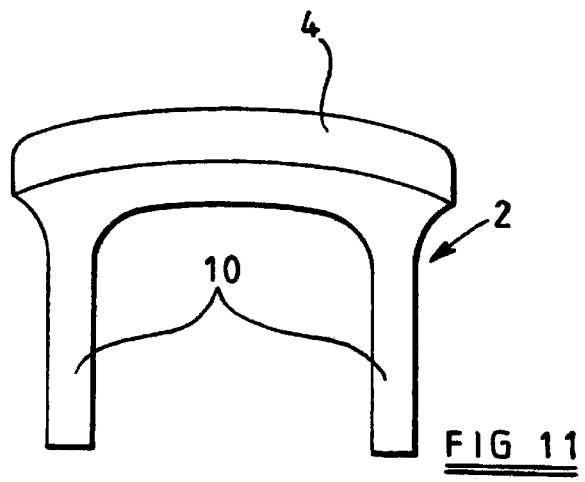

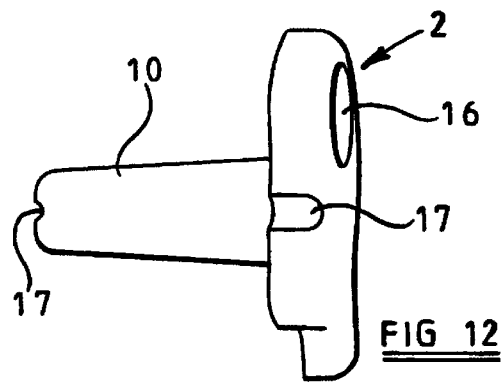
FIG 12
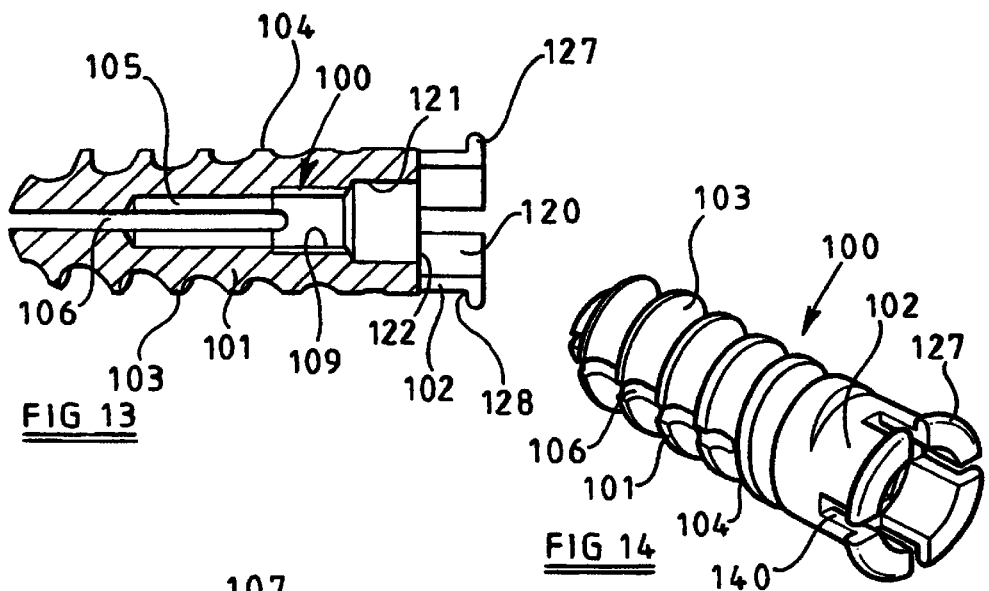
FIG 13
FIG 14
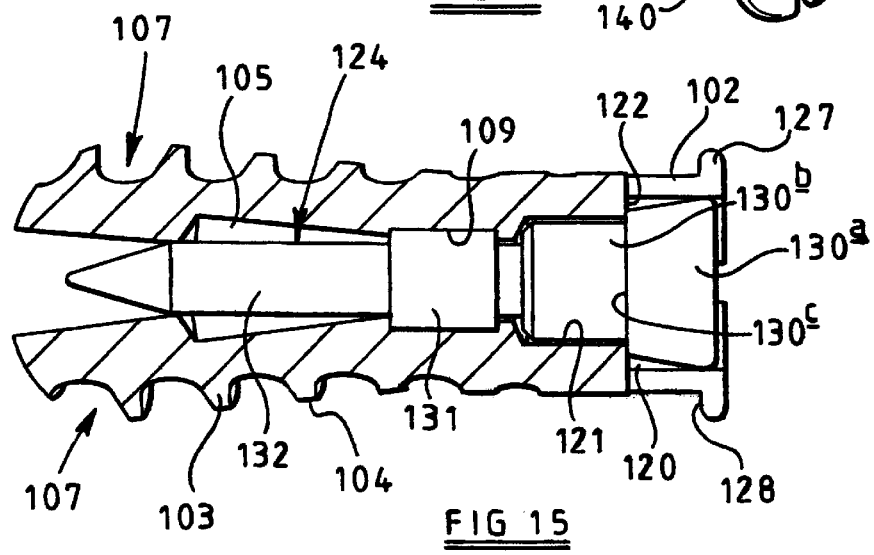
FIG 15

SURGICAL IMPLANT AND SURGICAL FIXING SCREW

The present invention relates, in a first aspect, to a surgical implant for use with a bone graft between vertebrae, more particularly cervical vertebrae, in order to fuse said vertebrae, to a system comprising said implant and to a method of facilitating the fusion of adjacent vertebrae using said system.

The present invention also relates, in a second aspect, to a surgical fixing screw which may be used for surgical applications generally, but which is particularly suitable for use with the surgical implant according to the first aspect of the invention.

With regard to said first aspect of the present invention, in certain spinal disorders, such as degenerative disease of the intervertebral substance (hereinafter simply referred to as "disc"), it is necessary for the disc to be removed and the neighbouring vertebrae to be fused, aided by a bone graft inserted between the vertebrae. Inevitably, the fusion process is slow, and it is desirable for the bone graft and vertebrae to be immobilised for fusion to take place with the vertebrae and graft correctly positioned.

One solution (exemplified by the so-called Cervical Spine Locking Plate System, available from Synthes) is to insert the bone graft between the vertebrae and then secure the vertebrae to each other by means of a metal plate which lies along one face (generally the anterior face) of the vertebrae. The plate is held in place against the vertebrae by fixing screws which pass through holes provided in the plate and which are screwed into holes drilled into the vertebrae. The bone graft is maintained in position by compressive forces. In use, however, such a plate can be difficult to align properly.

In another system (Fournitures Hospitalieres) a metal plate is integrally formed with a metal ring which protrudes perpendicularly from the midpoint of the plate. The plate can be supplied with a disc of hydroxy-apatite bone substitute fixed in the region enclosed by the ring. The ring containing the hydroxy-apatite disc is inserted between the vertebrae which presents the metal plate in the correct alignment for securing to the vertebrae by means of fixing screws. Alternatively, the plate is supplied without the disc of hydroxy-apatite and the surgeon prepares the bone graft. Difficulties arise if it is necessary to remove the plate, since the entire bone graft will also be removed, requiring the whole procedure to be repeated.

The latter system is not suitable for fusing three adjacent vertebrae.

It is an object of the first aspect of the present invention to provide a surgical implant which facilitates the fusion of adjacent cervical vertebrae, and obviates or mitigates the abovementioned problems.

According to said first aspect of the present invention, there is provided a surgical implant comprising:
(i) a body portion having first and second passages therethrough, said passages being adapted and disposed in said body portion so as to be capable of receiving a securing element (e.g. a screw) for securing said implant to first and second adjacent vertebrae (eg cervical vertebrae) respectively; and
(ii) first and second mutually spaced arms carried by and extending away from said body portion;
wherein said arms are adapted so as to be capable of insertion between said first and second adjacent vertebrae, and wherein at least part of said body portion is adapted to engage with anterior faces of both adjacent vertebrae when said arms are located between said adjacent vertebrae, so that, in use, a bone graft can be held in position between the first and second arms and between mutually facing superior and inferior surfaces of said first and second adjacent vertebrae.

Preferably, the body portion of the implant is constructed such that when the arms of the implant are located between said first and second adjacent vertebrae, another implant can be secured to the anterior face of one of the first and second adjacent vertebrae and a third vertebra, said third vertebra being adjacent to the same one of said first or second adjacent vertebrae.

The arms are preferably straight and preferably also mutually parallel.

Preferably, upper and lower surfaces of each arm are roughened and/or provided with a hydroxy-apatite coating. In use, said surfaces will be in contact with the facing superior and inferior surfaces of the adjacent vertebrae. The roughened surface and/or hydroxy-apatite coating encourages in-growth of bone, thereby providing additional securement of the implant.

The body portion may be provided with more than two passages. Most preferably three or four passages are provided. At least one passage preferably has its axis inclined to the arms. More preferably, at least said first and said second passages have mutually inclined axes.

Preferably, the implant is of a unitary construction of biocompatible material. Examples of suitable materials include titanium, titanium alloy and stainless steel.

Also according to said first aspect of the present invention, there is provided a system for fusing adjacent vertebrae (eg cervical vertebrae), said system comprising at least one surgical implant in accordance with said first aspect, at least one bone graft and securing elements for securing the implant to adjacent vertebrae.

Also according to said first aspect of the present invention, there is provided a method of fusing adjacent vertebrae (eg cervical vertebrae) comprising the steps of:
(i) introducing bone graft material between first and second adjacent vertebrae,
(ii) locating the arms of a surgical implant in accordance with said first aspect around said bone graft material and between said adjacent vertebrae,
(iii) securing at least one securing element into the first vertebra, and
(iv) securing at least one securing element into the second vertebra, wherein each securing element passes through a respective one of said passages in the body portion of the implant.

The method may be extended to the fusion of a third vertebra, said third vertebra being adjacent to one of said first and second adjacent vertebrae, in which case the above steps are repeated with respect to the first and third vertebrae or the second and third vertebrae using another surgical implant.

Preferably, said securing elements are fixing screws of which at least one may be a surgical fixing screw according to said second aspect of the present invention.

With regard to said second aspect of the present invention, it is an objection to provide a design of surgical fixing screw which enables a secure fixing of a part such as an implant to take place with a reduced risk of disengagement from such part.

According to said second aspect of the present invention, there is provided a surgical fixing screw including a head and a screw-threaded shank, wherein the head is formed so that it can be transformed between a laterally expanded condition and a laterally contracted condition.

The term "laterally" means laterally relative to the longitudinal axis of the shank. Preferably, the head is formed so that it can be transformed between a radially expanded condition and a radially contracted condition.

Preferably, the surgical fixing screw further includes retaining means engageable within the head for preventing the head from being transformed into its laterally contracted condition.

When in its laterally contracted condition, the surgical fixing screw can be inserted within an aperture in the part to be secured. When in its outwardly extended condition, the head of the surgical fixing screw enables fixing of the screw within the aperture in the part in a manner such as to reduce the risk of disengagement of the surgical fixing screw from the part.

In a preferred embodiment, the head is shaped so that, in its laterally expanded condition, it projects laterally into an undercut recess in the part whereby the head is prevented from disengagement from the part by interlocking with the latter.

Preferably, the head of the surgical fixing screw has a recess therein in which the retaining means is engageable so that the retaining means engages a wall of the recess to prevent the head from being transformed into its laterally compressed condition.

Also according to said second aspect of the invention, there is provided a surgical fixing screw comprising a head and an externally screw-threaded shank which is divided longitudinally into lateral wings which are capable of being deformed outwardly of the longitudinal axis of the shank. This obviates or mitigates the risk of the screw becoming detached from, or loosened in, a hole in bone or hard tissue in which the screw shank is engaged in use.

Conveniently, the shank is adapted to receive an expansion means which, during insertion into the fixing screw, causes the outward deformation of the wings. Desirably, the body of the shank tapers inwardly away from the head.

Preferably, the expansion means is held within the shank by means of a complementary thread arrangement.

Most preferably, the expansion means for causing outward deformation of the wings and the retaining means for the head are provided as different parts of a single retaining and expansion element engageable with the shank and the head of the screw.

Preferably, the surgical fixing screw is constructed and adapted for use in the securing of a surgical implant in position.

The head of the screw may have a first formation for engagement, in use, by a screwdriver and a second formation, spatially distinct from the first formation, for engagement, in use, by an alternative screwdriver. Thus, in the event that one of the first and second formations becomes damaged during insertion or removal of the screw using the appropriate screwdriver, the screw can be removed subsequently using the other screwdriver on the other of the first and second formations.

Desirably, said first and second formations are spaced apart longitudinally in the axis of rotation of the surgical fixing screw.

Embodiments of the present invention will now be described, by way of example, with reference to the accompanying drawings in which:

FIG. 1 is a perspective view of a surgical implant in accordance with said first aspect of the present invention;

FIG. 2 is a plan view of the surgical implant shown in FIG. 1;

FIG. 3 is an end-on view of the surgical implant shown in FIG. 1;

FIG. 4 is a cross-sectional view of the surgical implant shown in FIG. 1;

FIG. 7 is a axial section through the surgical fixing screw of FIG. 6;

FIG. 8 is a perspective view of the surgical fixing screw of FIGS. 6 and 7;

FIG. 9 is an end view of the head of the surgical fixing screw of FIGS. 6 to 8;

FIG. 10 is a side view of an expansion element for use in the fixing screw of FIGS. 6 to 9;

FIG. 11 is a plan view similar to FIG. 2 of another embodiment of surgical implant;

FIG. 12 is a side view of the implant of FIG. 11;

FIG. 13 is an axial section through an embodiment of surgical fixing screw for use with the implant of FIGS. 11 and 12;

FIG. 14 is a perspective view of the surgical fixing screw of FIG. 13;

FIG. 15 is an axial section showing the surgical fixing screw of FIGS. 13 and 14 with an inserted retaining and expansion element;

Figure 5:
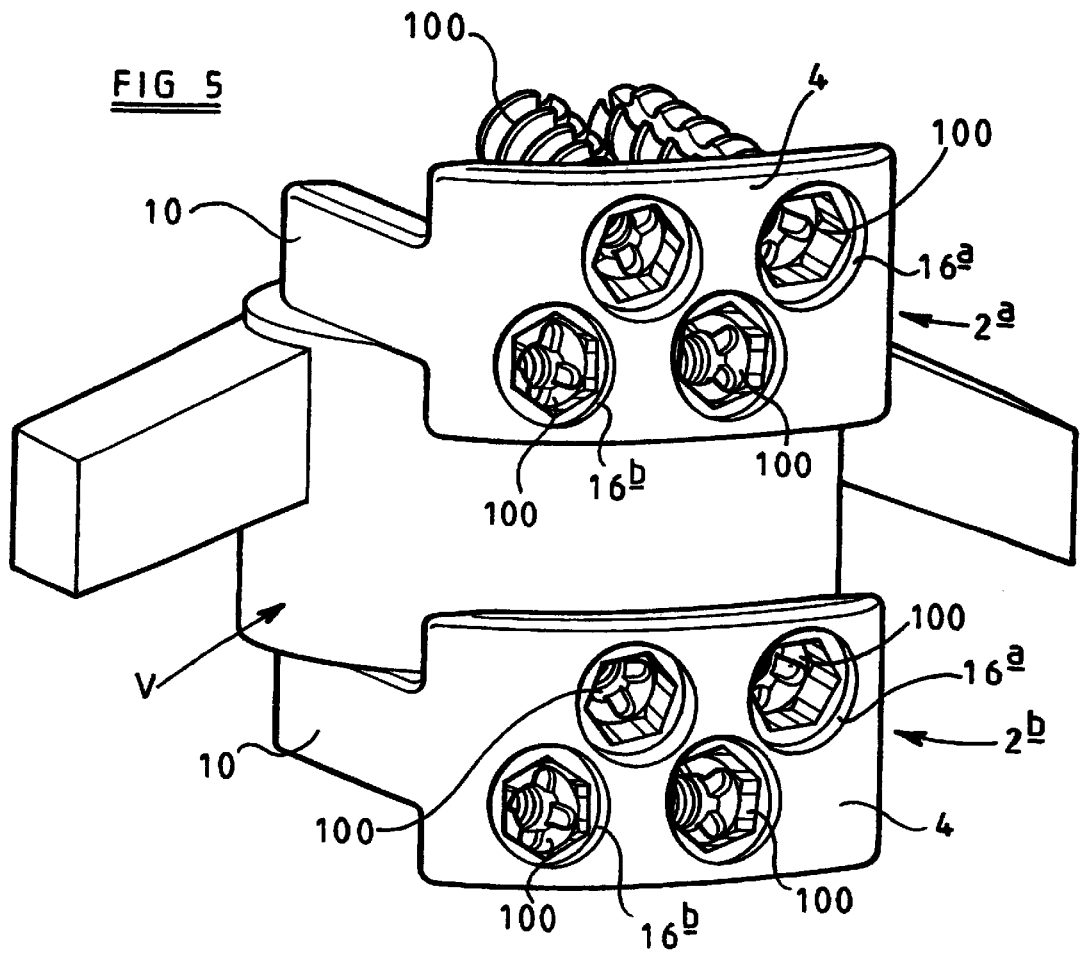
FIG. 5 is a schematic illustration showing the attachment of two surgical implants according to the present invention to a single cervical vertebra.
Figure 6:
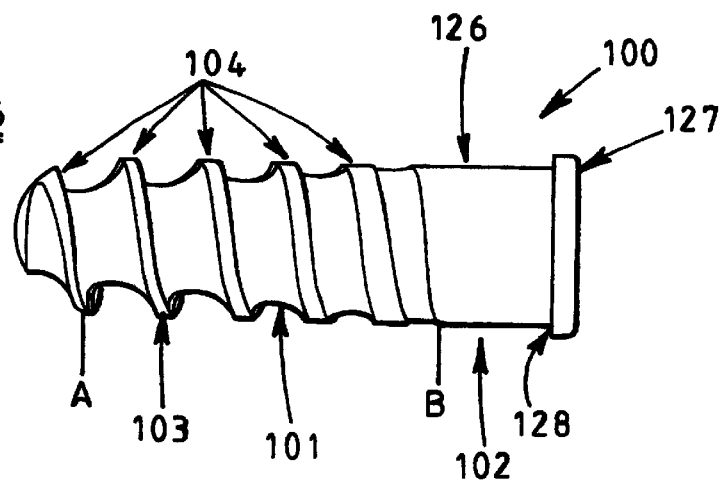
FIG. 6 is a side view of an example of a surgical fixing screw according to said second aspect of the present invention.

Referring to FIGS. 1 and 2, the surgical implant 2 is U-shaped and comprises a curved flange-like body portion 4 having a posterior major surface 6a, an anterior major surface 6b, a superior edge surface 8a and an inferior edge surface 8b, and a pair of mutually spaced, parallel straight arms 10. The implant 2 is of unitary construction and, in this embodiment, is made from titanium alloy (complying with BS7252 PT3 1990). At each opposite lateral end region of the body portion 4, a respective one of the arm 10 extends away from the body portion 4. The depth of the arms 10 (i.e. the distance between their upper surfaces 12a and lower surfaces 12b) is less than that of the body portion 4, such that upper end abutment surfaces 14a and lower end abutment surfaces 14b are defined on the body portion 4. The superior and inferior surfaces 12a, 12b of each arm 10 are roughened and provided with a hydroxy-apatite coating (not shown). The body portion 4 is provided with two pairs of identical passages 16a and 16b which extend through the body portion 4 from the posterior major surface 6a to the anterior major surface 6b of the body portion 4.

Referring to FIGS. 3 and 4, the passages 16a are spaced apart along the body portion 4 at a distance from the superior edge surface 8a of the body portion 4, while the passages 16b are at the same distance from the inferior edge surface 8b of the body portion 4 and offset relative to the first passages 16a. Each passage 16a, 16b comprises anterior and posterior coaxial cylindrical regions 18a, 18b of different diameters such that an annular step 20, which serves as a seat for a fixing screw, is defined at their intersection. The axis of each of the passages 16a is inclined above the direction of extent of the arms 10 by 10°. The axis of each of the passages 16b is inclined below the direction of extent of the arms 10 by 10°.

The surgical implant 2 may be used in an operation where, for whatever reason, it is necessary to replace the intervertebral disc between a pair of adjacent cervical vertebrae by a bone graft. In such an operation, the disc (or fragments thereof) is removed and the inferior surface of a first (superior) disc and the superior surface of an adjacent second (inferior) disc are prepared for the reception of a bone graft. Bone graft material is compacted between the vertebrae and the arms 10 of the implant 2 are pushed between the vertebrae, either side of the bone graft material, from the anterior side of the vertebrae. The respective regions of the posterior major surface 6a abut the anterior surfaces of the first and second vertebra.

The fact that the arms 10 of the implant 2 are located between the vertebrae ensures that there is no error in the alignment of the implant 2 before it is fixed in place. Such fixing is achieved by forming holes in the vertebrae using the passages 16 in the body portion 4 as guides, followed by inserting expanding surgical fixing screws, for example surgical fixing screws 100 as described below, through each passage 16a, 16b in the body portion 4 and into the respective vertebra.

In cases where two or more consecutive discs must be removed, it is possible to repeat the above procedure relative to one of the first and second vertebrae and a superior or inferior adjacent third vertebra using a second implant, and so on. It should be noted that the offset positioning of the passages 16a, 16b ensures that the screws used to fix the respective first and second implants do not interfere with each other. This is illustrated in FIG. 5, where it can be seen that the design of the implant is such that two identical implants 2a and 2b can be secured to a single vertebra V using the two intermediate pairs of screws 100 which are mutually offset because of the positioning of the passages 16a, 16b. It will be understood that the vertebrae (not shown in FIG. 5) which are adjacent to the illustrated vertebra V will be respectively secured by upper and lower pairs of screws 100 illustrated in FIG. 5.

Each surgical fixing screw 100 is tightened until the head of the screw is seated against the annular step 20, at which point the vertebrae are securely fixed relative to each other. The fixing in place of the implant 2 is enhanced by the inclination of the passages 16 in the body portion 4, which makes it more difficult for the implant 2 to work loose than if the passages 16a, 16b were mutually parallel or parallel to the direction of extent of the arms 10. The expanding nature of the screws 100 also assists in ensuring a secure fixing of the implant in place. Once in place, the roughened and hydroxy-apatite coated superior and inferior surfaces 12a, 12b encourage in-growth of bone on those surfaces 12a, 12b of the arms 10 only.

In the above-described procedure, it is generally intended for the implant 2 to remain permanently in place, however, there may be circumstances in which it is necessary for it to be removed. Should this be necessary, the implant 2 can be withdrawn by unscrewing the screws 100 and withdrawing the implant. Clearly, any bonding between the upper and lower surfaces 12a, 12b of the arms with the vertebrae must be broken, but the bone graft between the arms 10 will remain intact. Thus, replacement or permanent removal of the implant 2 can be achieved without requiring a second bone graft.

Referring now to FIGS. 6 to 9, the surgical fixing screw 100 comprises two parts, a shank 101 and a head 102. The shank 101 has an exterior screw thread 103 such that the body of the shank 101 decreases in diameter away from the head 102. The flight 104 of the screw thread 103 is, however, of constant diameter over the region AB, decreasing in diameter in only the terminal turn adjacent A. The flight 104 has a flat crest which increases in width towards the head 102 over the region AB. A passage 105 extends longitudinally throughout the length of the fixing screw 100. Two diametrically opposed slots 106 extend radially inwardly from the peripheral surface of the shank 101 to communicate with the passage 105. The slots 106 and passage 105 extend over the length of the shank 101 so as to divide the latter longitudinally into two lateral wings 107.

The passage 105 comprises three parts, a tapered end region 108, an intermediate screw-threaded region 109 and a head end region 120. The head end region 120 defines an internal recessed hexagonal formation 121 which opens onto the head end of the screw 100 and which, in use, engagingly receives a screwdriver having a hexagonal bit (not shown).

A step 122 is defined at the junction between the regions 109 and 120 which are situated within the head 102 of the screw 100. The step 122 faces the head end of the screw and has a cross-recessed formation 123 therein which, in use, engagingly receives another screwdriver having a cross-headed bit (not shown). It will therefore be understood that the formations 121 and 123 are spatially distinct (in this embodiment, they are spaced apart along the longitudinal axis of the screw) and are independently engageable by the respective screwdrivers.

The screw-threaded region 109 is adapted to receive an expansion element 124 (FIG. 10) which will be described later.

The tapered end region 108 of the passage 105 tapers inwardly away from the intermediate screw-threaded region 109 and extends over the whole of the length of the shank 101.

The head 102 has an outer peripheral surface 126 provided with a radial lip 127 so as to form an abutment shoulder 128 for engagement, in use, against the step 20 described above.

Referring now to FIG. 10, the expansion element 124 comprises a head region 130, an intermediate externally screw-threaded region 131 and a rod-like region 132. The head region 130 has a slot 133 for cooperative engagement by a further screwdriver bit. The intermediate screw-threaded region 131 is engageable with the internal screw-threaded region 109 such that the expansion element 124 can be fixed within the passage 105. The rod-like region 132 projects from the threaded region 131 and has a diameter larger than the minimum diameter of the tapered region 108.

In order to effect engagement of the fixing screw 100 in bone, a borehole is drilled in the latter and the screw 100 is secured in the borehole by rotating it using the hexagonal or cross-recessed formations 121 or 123 with the appropriate screwdriver. Then, the expansion element 124 is inserted into the screw 100 and is rotated using the further screwdriver bit engaged in the slot 133.

When the expansion element 124 is fully engaged within the passage 105, the action of the rod-like region 132 upon the internal surfaces of the tapered region 108 of the passage 105 deforms the lateral wings 107 outwardly, thus locking the screw 100 in the borehole and inhibiting backing out or loosening of the fixing screw 100.

If necessary, the fixing screw 100 can be extracted from the bone, after removal of the expansion element 124, by use of a suitable screw driver engaged with either of the formations 121, 123. This allows the option of choosing one specific formation 121 or 123 should the alternative formation 123 or 121 become damaged or otherwise unserviceable. This choice is especially advantageous as the lateral wings 107 will remain deformed after the removal of the expansion member 124 and therefore an effective engagement of the screwdriver with the chosen formation is essential.

The above described surgical fixing screw 100 may be used for other surgical applications.

Referring now to FIGS. 11 and 12, the surgical implant 2 is, like that of FIGS. 1 to 5, for fusing adjacent cervical vertebrae together, and similar parts are accorded the same reference numerals. In this embodiment, however, the arms 10 are not disposed at opposite lateral ends of curved flange-like body portion 4 but are spaced slightly inwardly of the ends. Also, as can be seen from FIG. 12, the superior and inferior surfaces of the arms 10 are not mutually parallel but are mutually tapered. This tapering is chosen so as to restore and/or maintain cervical lordosis (natural curvature of the spine). The lateral surfaces of the arms 10 are, however, mutually parallel as in the case of the embodiment of FIGS. 1 to 4.

A variety of implants 2 of different size may be provided with the arms 10 available in varying heights and widths to fit different anatomies.

Notches 17 are provided in the ends (lateral faces) of the body portion 4 and on the free ends (posterior faces) of the arms 10. These notches 17 enable the surgeon to tie a suture around the implant in order to hold the bone graft in position during insertion.

Figure 17:
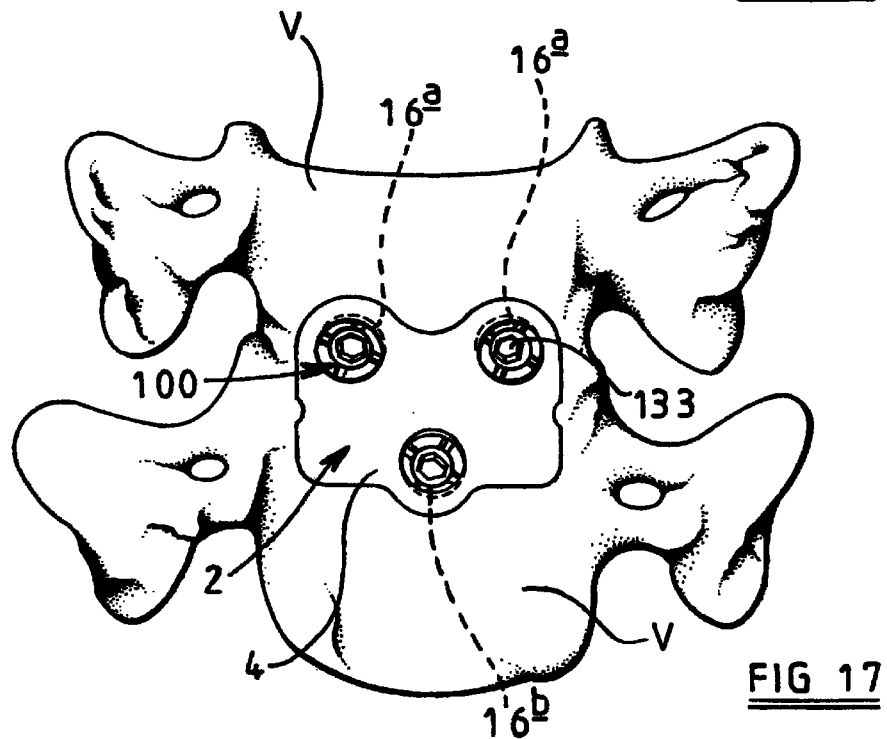
FIG. 17 is a view showing the use of the implant of FIGS. 11 and 12 and surgical fixing screws of FIGS. 13 to 15 to secure two cervical vertebrae together.

As can best be seen from FIG. 17, the superior and inferior faces of the body portion 4 are formed with complementary recesses and lugs to enable adjacent implants to be stacked closely together. In this embodiment, the implant 2 has two superior apertures 16a and one inferior aperture 16b.

Figure 16:
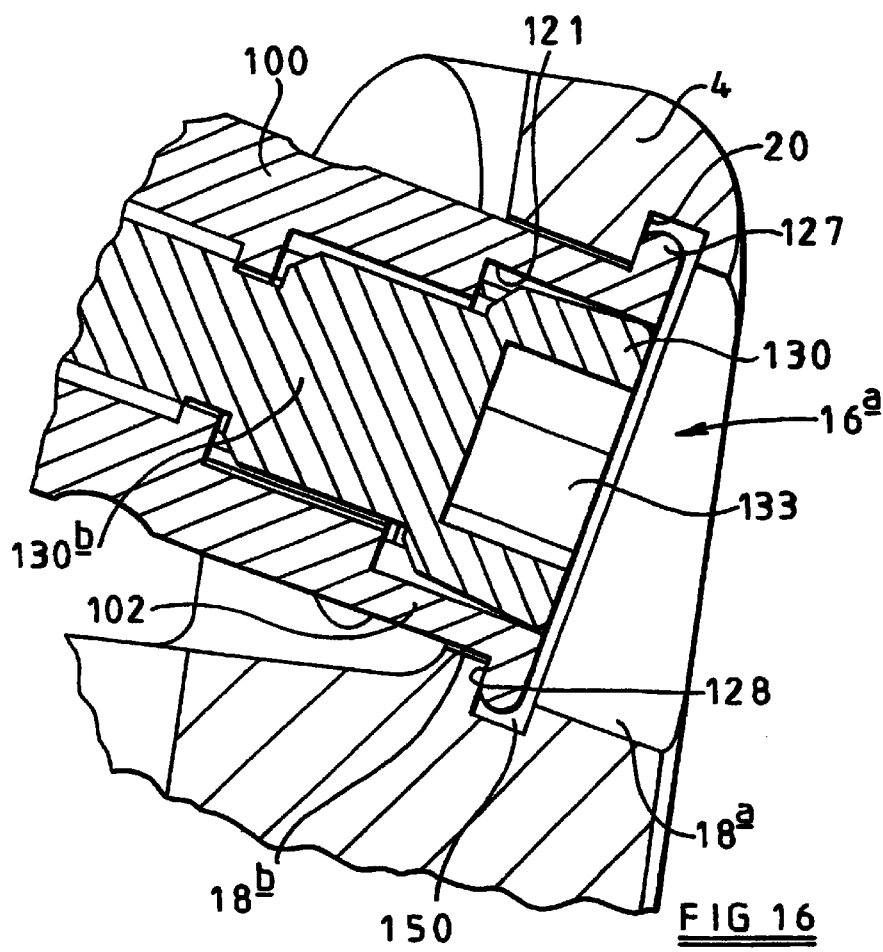
FIG. 16 is a detail showing the interengagement between the screw of FIG. 15 and the implant of FIGS. 11 and 12.

Referring now to FIGS. 13 to 15, surgical fixing screw 100 is similar to that of FIGS. 6 to 10 and similar parts are accorded the same reference numerals. In this embodiment, however, head 102 has a series of four equi-angularly spaced slots 140 extending from the outside of the head 102 to open into the head end region 120 of the passage 105. These slots 140 permit the head to be transformed between a laterally relatively expanded condition as illustrated in FIGS. 14, 15 and 16 and a laterally relatively contracted condition (not shown). These slots 140 also enable a screwdriver with a cross-headed bit to be engaged with the head 102 of the screw 100. Internal recessed hexagonal formation 121, in this embodiment, is disposed within the region of the shank 101 adjacent the head 102 rather than within the latter.

In this embodiment, the passage 105 does not extend over the full length of the shank 101 but terminates at a conical end wall spaced from the free end of the shank. The slots 106 extend over part of the length portion 108 of the passage 105 to the free end of the shank 101. Also, the portion 108 of the passage 105 is not tapered but is parallel sided.

The head region 130 of the expansion element 124 comprises an inwardly tapering frustoconical head portion 130a and a cylindrical head portion 130b. The frustum of the head portion 130a has a larger diameter than the adjacent head portion 130b so that a step 130c is defined between these two portions. The head portion 130b is of a size such that it is rotatable with clearance within the hexagonal formation 121. The base of the frusto-conical head portion 130a is equal in diameter to that of the head end region 120 of the passage 105 when the head is in its laterally expanded condition.

Referring now to FIG. 16, the surgical fixing screw 100 described above in relation to FIGS. 13 to 15 is mainly intended to be used with the surgical implant described above in relation to FIGS. 11 and 12. However, it does have other potential surgical uses. The anterior region 18a of each passage 16a or 16b has a diameter which is slightly less than that of the radial lip 127. Adjacent to the anterior region 18a of the passage 16, there is an undercut annular recess 150 following which the posterior region 18b of the passage 16 is provided. The posterior region 18b has a diameter which is marginally greater than the outer diameter of the head 102 of the screw 100.

In order to secure the implant 2 in position, a hole is drilled into the respective cervical vertebra through each aperture 16a, 16b. Then, each fixing screw 100 is inserted through the respective aperture 16a or 16b and rotated to cause it to advance into the hole in the cervical vertebra until the lip 127 engages against the body portion 4 around the anterior end of the passage 16. Because the lip 127 is curved, the head 102 is deformed radially inwardly into its laterally contracted condition as permitted by the partial closure of the slots 140. This allows the lip 127 to pass through the anterior region 18a and into the recess 150. When it reaches the recess 150, the head 102 is free to spring outwardly so that the lip 127 extends into the recess 150, thereby providing an interlock to prevent unwanted disengagement of the lip 127 from the undercut recess 150. The screw 100 can then be fully tightened to urge the implant against the cervical vertebrae. Then, the expansion element 124 is inserted into the screw 100 and rotated so as to cause the wings of the screw to be expanded outwardly to anchor the screw within the hole drilled in the cervical vertebra. At the same time, the head region 130 of the expansion element 124 enters the recess 120 fully and serves to retain the head 102 against being compressed radially inwardly. The head portion 130a may also serve to urge the head portion 102 outwardly if any permanent deformation of the head of the screw has taken place as a result of the lip 127 being forced through the smaller diameter anterior region 18a of the passage 16. In this way, the screw 100 is securely interlocked with the body portion 4 of the surgical implant 2.

FIG. 17 shows the arrangement where three screws 100 are used to secure the surgical implant 2 in position, with two of the screws being engaged with the upper cervical vertebra V and one screw being engaged with the lower cervical vertebra V of the pair to be fused together. The superior and inferior faces of the body portion 4 of the implant 2 are suitably shaped with a lug and recess arrangement to enable each portion 4 to be nested closely with the body portion(s) 4 of adjacent implant(s) 2.

What is claimed is:

1. A surgical implant comprising:
 a body portion having first and second passages therethrough, each of said passages being adapted and disposed in said body portion so as to be capable of receiving a securing element for securing said implant to first and second adjacent vertebrae respectively; and
 first and second mutually spaced arms carried by and extending away from said body portion;
 wherein said arms are adapted so as to be capable of insertion between said first and second adjacent vertebrae, and wherein said body portion comprises profiled surfaces for engagement with corresponding anterior faces of both adjacent vertebrae when said arms are located between said adjacent vertebrae, so that, in use, a bone graft can be held in position between the first and second arms and between mutually facing superior and inferior surfaces of said first and second adjacent vertebrae.

2. A surgical implant as claimed in claim 1, wherein the body portion is constructed such that, when the arms are located between said first and second adjacent vertebrae, another implant can be secured to the anterior face of one of the first and second adjacent vertebrae and a third vertebrae, said third vertebrae being adjacent to the same one of said first or second adjacent vertebrae.

3. A surgical implant as claimed in claim 1, wherein the arms are straight and mutually parallel.

4. A surgical implant as claimed in claim 3, the arms having superior and inferior surfaces for engaging corresponding surfaces of said adjacent vertebrae, wherein the arms between said superior and inferior surfaces are mutually tapered away from said body portion.

5. A surgical implant as claimed in claim 1, wherein the body portion is provided with more than two passages.

6. A surgical implant as claimed in claim 5, wherein said first and second passages are axially off-set relative to each other.

7. A surgical implant as claimed in claim 1, wherein at least one passage has its axis inclined to the arms.

8. A surgical implant as claimed in claim 1, wherein at least said first and said second passages have mutually inclined axes.

9. A surgical implant as claimed in claim 1, wherein at least one of said passages has an undercut recess therein.

10. A surgical implant as claimed in claim 1, wherein at least one of said passages comprises a portion for interlocking with an expandable portion of said securing element so as to prevent disengagement thereof.

11. A system for fusing adjacent vertebrae comprising:
at least one surgical implant having:
a body portion having first and second passages therethrough, each of said passages being adapted and disposed in said body portion so as to be capable of receiving a securing element for securing said implant to first and second adjacent vertebrae respectively; and
first and second mutually spaced arms carried by and extending away from said body portion;
wherein said arms are adapted so as to be capable of insertion between said first and second adjacent vertebrae, and wherein said body portion comprises profiled surfaces for engagement with corresponding anterior faces of both adjacent vertebrae when said arms are located between said adjacent vertebrae;
at least one bone graft for insertion between the first and second arms and between mutually facing superior and inferior surfaces of said first and second adjacent vertebrae; and
securing elements for securing the implant to said first and second adjacent vertebrae so that, in use, said bone graft can be held in position.

12. A method of fusing adjacent vertebrae comprising the steps of:
introducing bone graft material between first and second adjacent vertebrae,
providing a surgical implant comprising: a body portion having first and second passages therethrough, each of said passages being adapted and disposed in said body portion so as to be capable of receiving a securing element for securing said implant to first and second adjacent vertebrae respectively; and first and second mutually spaced arms carried by and extending away from said body portion; wherein said arms are adapted so as to be capable of insertion between said first and second adjacent vertebrae, and wherein said body portion comprises profiled surfaces for engagement with corresponding anterior faces of both adjacent vertebrae when said arms are located between said adjacent vertebrae,
locating the arms of said surgical implant around said bone graft material and between said adjacent vertebrae,
securing at least one securing element into the first vertebra, and
securing at least one securing element into the second vertebra,
wherein each securing element passes through a respective one of said passages in the body portion of the implant.

13. A surgical implant comprising:
a body portion having first and second passages therethrough, each of said passages being adapted and disposed in said body portion so as to be capable of receiving a securing element for securing said implant to first and second adjacent vertebrae respectively; and
first and second mutually spaced arms carried by and extending away from said body portion;
wherein said arms are adapted so as to be capable of insertion between said first and second adjacent vertebrae, and wherein at least part of said body portion is adapted to engage with anterior faces of both adjacent vertebrae when said arms are located between said adjacent vertebrae, so that, in use, a bone graft can be held in position between the first and second arms and between mutually facing superior and inferior surfaces of said first and second adjacent vertebrae and wherein said arms extend from said body portion so as not to enclose said bone graft so that said implant can be removed leaving said bone graft intact.

14. A surgical implant as claimed in claim 13, wherein the body portion is constructed such that, when the arms are located between said first and second adjacent vertebrae, another implant can be secured to the anterior face of one of the first and second adjacent vertebrae and a third vertebra, said third vertebra being adjacent to the same one of said first or second adjacent vertebrae.

15. A surgical implant as claimed in claim 13, wherein the arms are straight and mutually parallel.

16. A surgical implant as claimed in claim 15, the arms having superior and inferior surfaces for engaging corresponding surfaces of said adjacent vertebrae, wherein the arms between said superior and inferior surfaces are mutually tapered away from said body portion.

17. A surgical implant as claimed in claim 13, wherein the body portion is provided with more than two passages.

18. A surgical implant as claimed in claim 17, wherein said first and second passages are axially off-set relative to each other.

19. A surgical implant as claimed in claim 13, wherein at least one passage has its axis inclined to the arms.

20. A surgical implant as claimed in claim 13, wherein at least said first and said second passages have mutually inclined axes.

21. A surgical implant as claimed in claim 13, wherein at least one of said passages has an undercut recess therein.

22. A surgical implant as claimed in claim 13, wherein at least one of said passages comprises a portion for interlocking with an expandable portion of said securing element so as to prevent disengagement thereof.

* * * * *